United States Patent [19]

Jiang et al.

[11] Patent Number: 5,505,952
[45] Date of Patent: Apr. 9, 1996

[54] MODIFIED SYNTHETIC CROSS-LINKED AMINO ACID POLYMERS AND MEDICAL DEVICES FORMED THEREFROM

[75] Inventors: Ying Jiang, North Haven; Elliott A. Gruskin, Killingworth, both of Conn.

[73] Assignee: United States Surgical Corporation, Norwalk, Conn.

[21] Appl. No.: 229,970

[22] Filed: Apr. 19, 1994

[51] Int. Cl.$^6$ .............................. A61L 15/00; A61L 31/00
[52] U.S. Cl. ...................... 424/423; 424/447; 424/78.17; 424/445; 525/54.1; 525/54.11; 528/328
[58] Field of Search ................... 424/78.12, 78.17, 424/423, 445, 447; 525/54.1, 54.11, 328

[56] References Cited

U.S. PATENT DOCUMENTS

| | | |
|---|---|---|
| 3,810,468 | 5/1974 | Harper et al. . |
| 3,927,242 | 12/1975 | Rembaum et al. ................... 428/411 |
| 3,948,863 | 4/1976 | Akamatsu et al. . |
| 4,111,859 | 9/1978 | Strop et al. ............................... 521/33 |
| 4,180,633 | 12/1979 | Dixon ...................................... 525/359 |
| 4,265,233 | 5/1981 | Sugitachi et al. . |
| 4,556,056 | 12/1985 | Fischer et al. . |
| 4,603,695 | 8/1986 | Ikada et al. . |
| 4,674,488 | 6/1987 | Nashef et al. . |
| 4,713,244 | 12/1987 | Bawa et al. . |
| 4,772,284 | 9/1988 | Jefferies et al. . |
| 4,783,337 | 11/1988 | Wong et al. . |
| 4,840,626 | 6/1989 | Linsky et al. . |
| 4,911,926 | 3/1990 | Henry et al. . |
| 4,997,425 | 3/1991 | Shioya et al. . |
| 5,010,167 | 4/1991 | Ron et al. . |
| 5,035,893 | 7/1991 | Shioya et al. . |
| 5,092,884 | 3/1992 | Devereux et al. . |
| 5,209,746 | 5/1993 | Balaban et al. . |

FOREIGN PATENT DOCUMENTS

| | | |
|---|---|---|
| 0262890 | 9/1987 | European Pat. Off. . |
| 0334046 | 2/1989 | European Pat. Off. . |
| 0372969 | 12/1989 | European Pat. Off. . |

*Primary Examiner*—Jeffrey Mullis

[57] ABSTRACT

Synthetic, cross-linked amino-acid containing polymers are useful in forming medical devices. The hydrogels of the invention are particularly useful in wound healing and anti-adhesion applications.

18 Claims, No Drawings

MODIFIED SYNTHETIC CROSS-LINKED AMINO ACID POLYMERS AND MEDICAL DEVICES FORMED THEREFROM

FIELD OF THE INVENTION

This invention relates generally to amino acid polymers. More specifically, this invention relates to modified, synthetic, cross-linked amino acid polymers which are useful in forming medical devices.

BACKGROUND OF THE INVENTION

Adhesion formation following surgery or trauma is generally considered to be undesirable. For example, adhesions that form in relation to intestinal surgery, e.g., bowel resection, hernia repair, etc. may cause obstruction of the intestine. Adhesions that form near a bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function.

Various methods and substances have been used in the hope of preventing postoperative adhesions. Certain drugs and suffactants have been suggested. For example, U.S. Pat. No. 4,911,926 is directed to adhesion prevention by application of aqueous and non-aqueous compositions of a polyoxyalkylene block copolymer to injured areas of the peritoneal or pleural cavity or organs situated therein subsequent to surgical injury.

Another approach to adhesion prevention involves application of a physical barrier at the area of surgical injury. U.S. Pat. No. 4,674,488 is directed to interposing a barrier layer of soft biological tissue, such as collagen, collagen-fabric films, collagen membranes, or reconstituted collagen or DACRON® mesh, at the interface of a bone fracture and the surrounding tissue. U.S. Pat. No. 4,603,695 is directed to a molded polymeric material for preventing adhesion of vital tissues. The polymeric material is made of a biodegradable and absorbable polymer such as certain polyesters, collagen, amino acid polymers and chitin and may be placed where there is a possibility of adhesion setting in.

Other materials have also been used to form physical barriers in an attempt to prevent adhesions, including silicone elastomers, gelatin films and knit fabrics of oxidized regenerated cellulose (hereinafter ORC). In some cases, it is suggested that heparin, heparinoid, or hexuronyl hexosaminoglycan be incorporated into a matrix of ORC fabric or other matrices of hyaluronic acid, cross-linked and uncross-linked collagen webs, synthetic resorbable polymers, gelatin films, absorbable gel films, oxidized cellulose fabrics and films which are fabricated into a form that is said to be drapable, conformable and adherent to body organs and substantially absorbable within 30 days. See, e.g., U.S. Pat. No. 4,840,626 or EPA Pub. No. 0 262 890 or EPA Pub. No. 0 372 969.

Physical barriers are also used to cover and protect wound sites. PCT/US91/08972 is directed to a surgical article having a bioabsorbable fibrous matrix in a laminar relationship with a bioabsorbable cell barrier sheet. U.S. Pat. No. 5,092,884 and EPA Pub. No. 0 334 046 are directed to a surgical composite structure having absorbable and nonabsorbable components which may be useful for repairing anatomical defects, e.g., preventing hernia formation in an infected area. The nonabsorbable portion of the composite acts as a reinforcement material. Ingrowth of natural tissue is said to be enhanced by controlled degradation of the absorbable portion. U.S. Pat. No. 5,035,893 relates to a wound covering composition having a sheet of biopolymeric material and a film of polyurethane resin. U.S. Pat. No. 4,997,425 relates to a wound dressing having two layers; namely a first layer to be place on the wound surface having pores of 20 to 500 μm in diameter and a second layer remote from the wound surface having pores not more than 20 μm in diameter. The dressing can be made of polyamino acids cross-linked with hexamethylene diisocyanate by drying with warm air and cooling suddenly to a frozen state.

SUMMARY OF THE INVENTION

It has now been found that synthetic cross-linked amino acid polymers are useful in forming medical devices. The term "synthetic" as used herein with respect to the polymers means synthesized rather than naturally occurring. The polymers of this invention are made at least in part from one or more amino acids having a pendant group which provides a site at which cross-linking may occur. Such pendant groups include hydroxyl, thiol, amino, phenoxyl and/or carboxyl pendant groups. Cross-linking of the amino acid polymers can be achieved by reacting them with a cross-linking agent such as a diol, diamine dihalo isocyanate, oxalyl chloride or succinyl chloride. Once cross-linked, the polymers form a water-swellable hydrogel.

In particularly useful embodiments, the amino acid polymers are modified by reacting, either before or after cross-linking, with a compound of the formula:

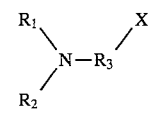

wherein X is halogen,

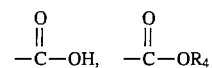

or anhydride and $R_1$, $R_2$, $R_3$ and $R_4$ are the same or different and are individually selected from the group consisting of straight or branched $C_1$-$C_7$ alkyl groups. Diethylchloroethyl amine is a particularly useful compound for reaction with amino acid polymer prior to cross-linking.

The polymers of this invention are useful in forming medical devices such as, for example, wound dressings and anti-adhesion materials.

DESCRIPTION OF PREFERRED EMBODIMENTS

The cross-linked amino acid polymers of this invention include polymer chains made at least in part from one or more amino acids having a pendant group which provides a site at which cross-linking of the polymer chains may occur. Such pendant groups include, for example, hydroxy, thiol, amino, phenoxyl and/or carboxyl groups. Suitable amino acids include, for example, serine, threonine, aspartic acid, glutamic acid, arginine, lysine, cysteine, cystine, tyrosine and methionine, asparagine, glutamine, phenylalanine, tryptophan, proline and histidine. The precise composition of the polyamino acid chains may vary widely provided that a sufficient number of pendant group-containing amino acids are incorporated into the chain to provide the desired amount of cross-linking. The polymer chain may include a variety of amino acids, or other monomers in combination with amino acids. Such other monomers which may be employed include those known to provide absorbable polymers, such as, for example, glycolide, lactide, caprolactone, alkylene carbonates or alkylene oxides. Thus, the polyamino acid chain may be a homopolymer or copolymer (random, block or graft). The amount of pendant group-containing amino acids in the polyamino acid chains typically will range from about 5 to about 100%. A homopolymer of lysine is a particularly useful polyamino acid.

Methods of synthesizing polyamino acids are known to those skilled in the art. In addition, certain polyamino acids, such as poly(lysine), are commercially available.

Once tile synthetic amino acid polymer is obtained, it can be modified by reacting with a compound of the formula

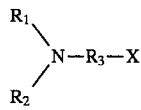

wherein X is halogen (e.g., Cl, Br, I),

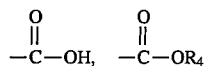

or anhydride and $R_1$, $R_2 R_3$ and $R_4$ are the same or different and are individually selected from the group consisting of straight or branched $C_1$–$C_7$ alkyl groups. Typically, the amount of the above-mentioned compound that is reacted with the amino acid polymer ranges from about 5 to about 100 mole percent, and preferably from about 5 to about 20 mole percent based on the amount of amino acid polymer present. A particularly useful compound for reaction with the amino acid polymer is diethyl chloroethyl amine.

The amino acid polymers are also cross-linked. Any known method of cross-linking the amino acid chains may be employed. For example, the polyamino acid chains may be reacted with a diol, diamine, di-acid, di-isocyanat, dihalo-isocyanate or derivatives thereof to provide cross-linking. A particularly useful cross-linking agents arc succinyl chloride and oxalyl chloride.

Typically, the amount of cross-linking agent reacted with the polyamino acid will range from about 5 to about 100 mole percent based on the weight of the amino acid polymer. Preferably, from about 5 to about 20 mole percent cross-linking agent is used.

The cross-linked polyamino acid normally forms a hydrogel which swells when exposed to water. The hydrogels may also be biodegradable, for example, by enzymatic action. The synthetic nature of the compositions of this invention allow the degradability of articles formed therefrom to be more accurately predicted compared to naturally occurring polyamino acids.

The cross-linked polyamino acid may be processed in any manner known to those skilled in the art for processing hydrogels. For example, the hydrogel may be soaked in aqueous solutions, dried, freeze-dried, ground or pulverized or mixed with other materials (absorbable or non-absorbable).

It is further within the scope of this invention to incorporate one or more medico-surgically useful substances into the present invention, e.g., those which accelerate or beneficially modify the healing process when particles are applied to a surgical repair site. So, for example, the hydrogel can carry a therapeutic agent which will be deposited at a repair site. The therapeutic agent can be chosen for its antimicrobial properties, capability form promoting repair or reconstruction and/or new tissue growth. Antimicrobial agents such as broad spectrum antibiotic (gentamycin sulphate, crythromycin or derivatized glycopeptides) which are slowly released into the tissue can be applied in this manner to aid in combating clinical and sub-clinical infections in a tissue repair site. To promote repair and/or tissue growth, one or several growth promotion factors can be introduced into the hydrogels, e.g., fibroblast growth factor, bone growth factor, epidermal growth factor, platelet derived growth factor, macrophage derived growth factor, alveolar derived growth monocyte derived growth factor, magainin, and so forth. Some therapeutic indications are: glycerol with tissue or kidney plasminogen activator to cause thrombosis, superoxide dimutase scavenge tissue damaging free radicals, tumor necrosis factor for cancer therapy or colony stimulating factor and interferon, interleukin-2 or other lymphokine to enhance the immune system. Optionally a dye or marker substance may also be incorporated into the hydrogel.

In order that those skilled in the art may be better able to practice the present invention, the following examples are given as illustrations of the preparation of a hydrogel in accordance with the present invention. It should be noted that the invention is not limited to the specific details embodied in the examples and further that all ratios or parts are by weight.

EXAMPLE 1

Polylysine (0.8 grams) is dissolved in 10 grams DMSO to obtain a clear solution. After two minutes of stirring, 0.08 grams of succinyl chloride is added, with continued stirring at room temperature. Two drops of pyridine are added after 10 minutes. The viscosity increases and after 20 minutes a gel is formed. The gel is placed in a vacuum oven and heated at 60° C. and 1 mmHg for 16 hours. The gel is then re-hydrated by putting it into a beaker containing 100 ml of water. The gel is recovered, ground in a tissue grinder, and freeze-dried.

The resulting gel powder may be used as is, or may be cast into a sheet or film. The gel is particularly suited for use as a wound healing agent to be applied to a wound or repair site or as an anti-adhesion agent by placing the gel between tissues within a mammalian body.

EXAMPLE 2

0.8 grams of the cross-linked gel obtained in Example 1 is "suspended in 20 ml of distilled water with stirring. A large excess (3.0 grams) of diethylchloroethyl amine in hydrochloric acid (DEAE-Cl.HCl) is then added to the suspension with continued stirring. 1.5 grams of NaOH is then added and stirring is continued for five hours at 60° C. The suspension is filtered to recover the gel and washed sequentially with distilled water, methanol and acetone. Upon drying, 0.8 grams of gel bearing diethylaminoethyl groups is recovered.

The reaction sequence for producing the modified cross-linked amino acid polymer of Example 2 can be schematically represented as follows:

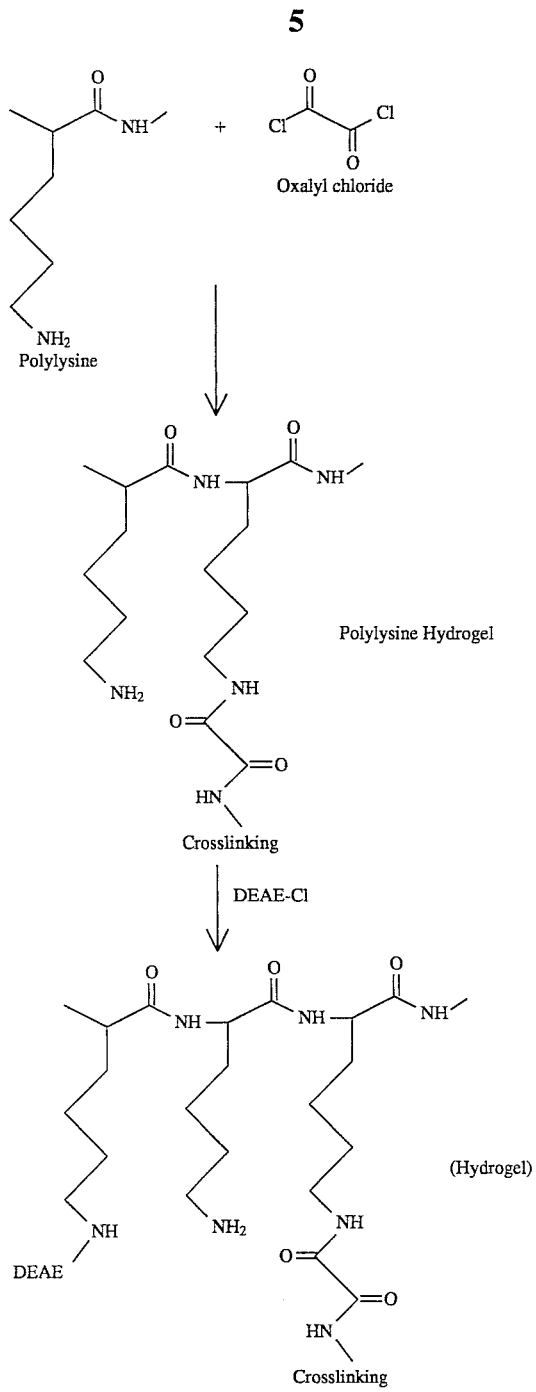

Obviously, other modifications and variations of the present invention are possible in light of the above teachings. It is therefore to be understood that changes may be made in particular embodiments of the invention described which are within the full intended scope of the invention as defined by the claims.

We claim:

1. A medical device comprising a synthetic cross-linked amino acid polymer, wherein said polymer includes one or more amino acids selected from the group consisting of serine, threonine, aspartic acid, glutamic acid, arginine, lysine, cystine, cysteine, tyrosine and methionine, said amino acid polymer further having at least one substituent attached to an amine group of the amino acid polymer, said substituent being provided by reacting the amino acid polymer with a compound of the formula

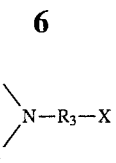

wherein X is Cl, Br, I,

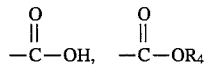

or anhydride and $R_1$, $R_2$, $R_3$ and $R_4$ are the same or different and are individually selected from the group consisting of straight or branched $C_{1-C7}$ alkyl groups.

2. A device as in claim 1, wherein said one or more amino acids is selected from the group consisting of lysine and glutamic acid.

3. A device as in claim 1, wherein said synthetic cross-linked amino acid polymer further comprises a cross-linking agent selected from the group consisting of diols, diamines, diacids, dihalo isocyanates, oxalyl chloride and succinyl chloride.

4. A device as in claim 1, wherein said synthetic cross-linked amino acid polymer comprises poly(lysine) chains cross-linked with oxalyl chloride.

5. A method of preparing a medical device comprising:

providing a polymer including one or more amino acids selected from the group consisting of serine, threonine, aspartic acid, glutamic acid, arginine, lysine, cystine, cysteine, tyrosine and methionine reacting the amino acid polymer with a compound of the formula

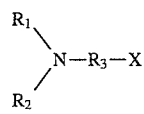

wherein X is Cl, Br, I

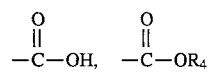

or anhydride and $R_1$, $R_2$, $R_3$ and $R_4$ are the same or different and are individually selected from the group consisting of straight or branched $C_{1-C7}$ alkyl groups;

cross-linking the polymer; and forming the cross-linked polymer into a medical device.

6. A method as in claim 5, wherein said cross-linking step comprises reacting the polymer with a member selected from the group consisting of diols, diamines, dihalo isocyanates, oxalyl chloride and succinic chloride.

7. A method as in claim 5, wherein said forming step comprises casting the cross-linked polymer to form a film.

8. A method as in claim 7, wherein the polymer provided is a synthetic poly(lysine) and the cross-linking step comprises reacting the polylysine with oxalyl chloride.

9. A method of preventing adhesions from forming between two tissues within a mammalian body, the method comprising:

providing a device made from a synthetic cross-linked amino acid polymer by providing a polymer including one or more amino acids selected from the group consisting of serine, threonine, aspartic acid, glutamic acid, arginine, lysine, cystine, cysteine, tyrosine and methionine, reacting the polymer with a compound of the formula

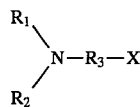

wherein X is Cl, Br, I,

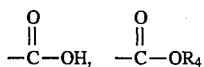

or anhydride and $R_1$, $R_2$, $R_3$ and $R_4$ are the same or different and are individually selected from the group consisting of straight or branched $C_{1-C7}$ alkyl groups, and cross-linking the polymer; and placing the device within the body, between the two tissues.

10. A method as in claim 9, wherein said step of cross-linking the polymer comprises reacting the polymer with a cross-linking agent selected from the group consisting of oxalyl chloride, succinyl chloride, diols, diamines, acids, dihalo isocyanates and their derivatives.

11. A method as in claim 9 wherein the polymer is poly(lysine) and the cross-linking agent is oxalyl chloride.

12. A method as in claim 9, wherein the device is provided in the form of a powder, sheet, film or pad.

13. A method as in claim 9 wherein said reacting step is performed prior to said cross-linking step.

14. A method of promoting healing at a wound or tissue repair site comprising:

providing a device made from a synthetic cross-linked amino acid polymer by providing a polymer including one or more amino acids selected from the group consisting of serine, threonine, aspartic acid, glutamic acid, reacting the polymer with a compound of the formula

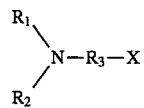

wherein X is Cl, Br, I,

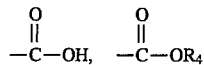

or anhydride and $R_1$, $R_2$, $R_3$ and $R_4$ are the same or different and are individually selected from the group consisting of straight or branched $C_{1-C7}$ alkyl groups, and cross-linking the polymer; and applying the polymer to the wound or tissue repair site.

15. A method as in claim 14, wherein said step of cross-linking the polymer comprises reacting the polymer with a cross-linking agent selected from the group consisting of oxalyl chloride, succinyl chloride, diols, diamines, acids, dihalo isocyanates and their derivatives.

16. A method as in claim 15, wherein the polymer is poly(lysine) and the cross-linking agent is oxalyl chloride.

17. A method as in claim 14, further comprising the step of incorporating a therapeutic agent into the polymer prior to said applying step.

18. A method as in claim 14 wherein said reacting step is performed prior to said cross-linking step.

* * * * *